(12) United States Patent
Nguyen-Dinh et al.

(10) Patent No.: US 7,588,540 B2
(45) Date of Patent: Sep. 15, 2009

(54) ULTRASONIC PROBE FOR SCANNING A VOLUME

(75) Inventors: An Nguyen-Dinh, Valleres (FR); Aimé Flesch, Andrésy (FR); Rémi Dufait, Tours (FR); Philippe Auclair, Tours (FR)

(73) Assignee: Vermon, Tours (FR)

( * ) Notice: Subject to any disclaimer, the term of this patent is extended or adjusted under 35 U.S.C. 154(b) by 734 days.

(21) Appl. No.: 11/101,526

(22) Filed: Apr. 8, 2005

(65) Prior Publication Data
US 2006/0241453 A1 Oct. 26, 2006

(51) Int. Cl.
*A61B 8/14* (2006.01)
(52) U.S. Cl. ..................................... 600/459
(58) Field of Classification Search ......... 600/437–472, 600/141; 310/330–334; 128/916; 367/7, 367/11, 130, 138
See application file for complete search history.

(56) References Cited

U.S. PATENT DOCUMENTS

| | | | | |
|---|---|---|---|---|
| 3,964,296 A | * | 6/1976 | Matzuk ....................... 73/607 |
| 5,152,294 A | * | 10/1992 | Mochizuki et al. .......... 600/459 |
| 5,159,931 A | | 11/1992 | Pini |
| 5,460,179 A | * | 10/1995 | Okunuki et al. ............. 600/444 |
| 5,782,769 A | * | 7/1998 | Hwang et al. ............... 600/454 |
| 6,203,498 B1 | * | 3/2001 | Bunce et al. ................ 600/446 |
| 6,264,607 B1 | * | 7/2001 | Goll et al. ................... 600/437 |
| 7,081,093 B2 | * | 7/2006 | Flesch ........................ 600/459 |
| 2005/0007882 A1 | * | 1/2005 | Bachelor et al. ............ 367/103 |
| 2006/0241453 A1 | * | 10/2006 | Nguyen-Dinh et al. ...... 600/445 |

* cited by examiner

*Primary Examiner*—Eric F Winakur
*Assistant Examiner*—Lawrence N Laryea
(74) *Attorney, Agent, or Firm*—Stites & Harbison PLLC; Ross F. Hunt, Jr.

(57) ABSTRACT

An ultrasonic imaging probe is provided which is capable of capturing "on-the-fly" scanning planes in successive positions of the probe so as to form a volumetric image representation at a real time frame rate. The probe includes a flexible sealing membrane for a coupling fluid. Laterally extending folding portions of the flexible membrane provide fluid isolation and cancellation of parasitic constraining forces normally generated during probe movement.

7 Claims, 3 Drawing Sheets

ULTRASONIC PROBE FOR SCANNING A VOLUME

BACKGROUND OF THE INVENTION

1. Field of the Invention

The invention relates to ultrasonic probes used for volumetric scanning and, more particularly, to an ultrasonic imaging probe capable of capturing "on-the-fly" scanning planes in successive positions so as to form a volumetric image representation at a real time frame rate.

2. Related Art

Ultrasonic scanners and probes for acquiring and processing volume information related to biologic tissue or a living body are well known in the art. In the early 1980s, the three-dimensional visualization of human fetus began using systems employing mechanical equipment and basic algorithms for volume rendering. It is believed that these systems are the first 3D imaging systems that use a linear array transducer mounted on a position-sensing arm and capable of providing the system with information regarding the spatial position of the transducer. This approach requires complex mechanical equipment and has now been abandoned by the industry in favor of more advanced 3D concepts including 2D array (matrix array) transducer systems and moving probe systems (employing a motorized linear array transducer).

The matrix array transducer systems are capable of scanning a volume of the region of interest without any movement of the sensing device. In this regard, because the elements of the array (i.e., the pixels) are regularly disposed on the surface of the transducer, a combination of selected pixels, and associated predetermined electronic delay lines for enabling the pixels to be controlled independently, enables focusing of the transducer on any location on the region of interest.

Although the first, matrix array approach definitely provides major advantages in comparison with moving probes, the design and assembly of matrix array transducer devices turns out to be quite intricate, especially in terms of the repeatability and homogeneity of the pixels. In the latter regard, several thousand pixels are necessary to achieve an acceptable image quality. Further, the synthetic acoustic apertures obtained from pixel combinations are of different homogeneities in different orientations. In addition, the required electrical matching of each pixel to the transmission line also presents problems. With regard to the associated imaging system for driving the matrix array transducer, this requires the development of a specific electronic mainframe providing a very large number of independent channels. Because of the high number of pixels to be controlled, the resultant mainframe design specifications rapidly push the limits of the available technologies in terms of component performance and miniaturization so that, currently, the matrix-based imaging systems are typically dedicated to research activities where issues of costs and intrinsic image quality can be balanced by scientific interests and educational considerations.

The second group of ultrasound instruments, i.e., the so called "moving probe" instruments, is theoretically more basic and can be considered to be an extension of the well known linear array transducer technology that operates on conventional or existing imaging systems. The ultrasound transducer used is very similar to conventional devices designed for 2D scanning operations, such as flat or curved linear arrays or phased arrays well known in the art. The transducer head of these instruments is mounted in a moving probe that also includes a mechanism for the transducer assembly including guiding and motorization means for moving the transducer probe during scanning operations. Since the probe uses a linear array transducer, imaging systems compatible with such a probe can be of conventional types and designs that are widely available commercially, and wherein minor upgrades have been implemented such as the addition of an add-on transducer interface and volume rendering software.

In theory, 3D scanning using a linear array transducer can be performed through transducer movements such as swinging, sliding or rotating. The movement can be an alternating movement (e.g., forward and backward) or continuous, and the amplitude of the transducer movement can extend over a range of from a few degrees to 180 degrees or more, depending on the requirements of the particular application. Because, in general, the construction of a 3D moving probe only requires an array transducer coupled to a suitable motorization means and sealed by a probe housing providing an acoustic window for enabling energy transmission to and from the region of interest, a number of different methods and devices are disclosed in the prior art that are usable for 3D scanning. However, in general, two transducer movements are preferred, viz., a rotational movement and a swinging movement.

More specifically, the rotating devices basically comprise phased array probes wherein the transducer footprint is small and the scanning geometry is of sector shape. It is noted that this group of probes is particularly well adapted for cardiology wherein a small emitting surface and sector scanning are required.

On the other hand, swinging probes have larger acoustic windows in order to carry out operations using a linear array transducer. With this type of probe, a synthetic image is obtained from the electronic driving of the elements of the array and, therefore, volume information is obtained by swinging of the array transducer in the elevation plane. This volume scanning method has the advantage of minimizing any encumbrance on the probe operation, and is capable of providing volume images of most human organs without moving the probe itself.

In practice, rotating and swinging probe devices are characterized by different design and assembly difficulties. For example, insofar as the moving transducer of the probe is required to be immersed in a coupling fluid so as to enable acoustic signals to be effectively received through the probe windows, the motorization means for the transducer must be assembled separately from the coupling chamber. This is done to prevent the fluid from causing problems with the operation of the motor and/or transmission. In the rotating devices, providing sealing of the motor from the transducer is quite straightforward. In this regard, an O-ring seal is usually disposed on the output shaft of the motor at the boundary thereof with the liquid chamber so as to provide liquid sealing of the motor.

On the other hand, with respect to swinging probe devices wherein a linear array is caused to laterally swing through an arc, the transducer is mounted on a swinging mechanism having an axis of rotation that is aligned with the azimuthal plane of the transducer. The rotation axis is then connected to the motor output so as to provide the desired swinging movement of the transducer. The coupling provided between the motor and the swinging mechanism can be provided by direct coupling, a pulley system or an intermediate gearbox. Since the rotation axis is azimuthally aligned, the separation between the wet chamber (i.e., the portion of the housing containing the coupling fluid) and the exterior becomes significantly greater than with previous devices.

Methods and devices for implementing 3D ultrasonic probes that have been disclosed in the prior art will be further described below to demonstrate the advantages and drawbacks of these prior art methods and devices.

For example, mechanically moving ultrasonic 3D/4D probes of interest are disclosed in U.S. Pat. No. 5,159,931 to Pini which relates to an apparatus for three-dimensional reconstruction of anatomic body. The apparatus comprises an ultrasonic mechanical probe wherein a sector scanning transducer is moved through an angle of 180 degrees in order to form a volume image. Rotation of the scanning plane can be achieved either mechanically, using a motor for rotating the transducer, or electronically, using a matrix transducer. The method of forming a 3D image is disclosed in the patent but no details are provided regarding the mechanical probe construction..

U.S. Pat. No. 5,152,294 to Mochizuki discloses a swinging ultrasonic apparatus for three-dimensional imaging. In this apparatus, a probe housing or casing receives a swinging mechanism for an ultrasonic array transducer, and a motorization means is provided for moving the transducer. A position coding device is used for sensing the transducer position during the operation thereof and for supplying this information to provide control of the system. The apparatus also comprises external shell that isolates the surface of the transducer from the body to be scanned. A coupling liquid is used for enabling the transmission of acoustic energy through the housing shell. A partition membrane is provided between a transducer end portion and the housing or case so as to hermetically retain the fluid coupling inside of the housing. In order to avoid any internal reflections of traveling echoes, the internal curvature of the housing or case is made larger than that of the transducer so as to direct reflected echoes to the bottom side of the housing or case at which an absorbent material is disposed.

The apparatus of the Mochizuki patent suffers important shortcomings with respect to the curvatures of the transducer and the case. In this regard, the non-uniform distance separating the transducer from the case shell strongly affects the homogeneity of the probe output. The amount of attenuation varies with the distance and the resultant impedance mismatches (sound speed and density) produce deviations in the transducer radiation pattern which contribute to an increase in side lobe levels and to focal aberrations. Further, the liquid partition membrane, which is provided as an add-on device over the front surface of the transducer, causes image artifacts and produces attenuation of the acoustic energy.

In the Mochizuki patent, the use of a loose membrane is proposed so as to allow the transducer to be swung with ease. The associated drawings indicate a "S" shaped membrane is provided for this purpose. As described, the partition membrane of the Mochizuki patent is compressed and released laterally aside from the transducer, during operation, thereby introducing a constraining force when the transducer is swung. This constraining force will result in non-uniform transducer movement so that the overall system must be implemented with a real time position correction algorithm. While a probe apparatus is well adapted for a conventional 3D imaging process wherein the transducer is incrementally stopped in a first position to effect acquisition of an image and then is stepped up to the next position to effect acquisition of a further image, this method is not, however, compatible with "on-the-fly" 3D imaging processing wherein the volumetric information is instantly available during probe operation and wherein the transducer movement must be accurately correlated with the images being acquired.

Turning to the available methods for providing liquid separation in mechanical ultrasonic devices, the use of a flexible membrane for sealing the coupling liquid bath against the external environment has been disclosed in the prior art at least since 1984. In this respect, Biophysic Medical, France proposed at that time a A-scan/B-scan ophthalmic scanner commercially designated as Ophtascan™. The scanner is typically equipped with a "B-mode" imaging mechanical probe so as to provide users with sector viewing of the organ. Probes that are compatible with such systems include a swinging transducer which is moved by motorization means connected thereto through a rotating/swinging movement transformation system. The transducer is equipped with a flexible membrane which is sealed, respectively, to the periphery of the transducer and to the probe housing, in order to provide separation of the fluid chamber. The flexible membrane is made from an elastomeric material (e.g., latex, silicon rubber, natural caoutchouc or the like) having a wave shape from the center to the periphery. The center of the membrane is provided with a hole that matches the transducer circumference and is bonded to that circumference. The periphery of the membrane is attached or sealed to the probe housing. When assembled, the transducer is capable of swinging movement over the operational amplitude thereof while compressing and releasing the membrane portion in the direction of movement.

The scanner proposed by Biophysic Medical is designed for moving single element devices wherein the diameter of the transducer is small enough, as compared with the dimensions of the membrane, to allow a swinging movement of the transducer within acceptable mechanical constraints. Because the membrane is mounted horizontally and secured to the diameter of the transducer, the mechanical effort that must be exerted to overcome the mechanical constraints varies with the position of the transducer. As a result, it is necessary to make corresponding corrections in the motor and in system operations.

Major drawbacks suffered by the Biophysic Medical scanner apparatus include, first, the assembly method required for attaching the membrane to the transducer case is unreliable and the resultant membrane attachment is subject to leaking of the fluid. Second, the required positioning of the membrane increases the effort that must be provided by the motor when the transducer reaches the extreme positions of the swinging movement thereof. Moreover, these observations are also relevant to the apparatus disclosed in the Mochozuki patent wherein a similar membrane is assembled and used therein..

With respect to the prior art discussed above and the method of making 3D ultrasonic probes herein described, there is obviously a need to improve existing 3D probe constructions and manufacturing methods in order to provide better reliability and performance.

SUMMARY OF THE INVENTION

One principal object of the present invention is to provide a 3D ultrasonic probe incorporating, internally mounted therein, a swinging linear array transducer which has the capability of providing volume information acquisition in a real time operation.

A further principal object of this invention is to provide a novel transducer assembly which is suitable for real time volume acquisition operations and which incorporates a low friction scanning 3D probe having a sealed liquid bath for providing coupling of ultrasound energy to the transducer.

One aspect of the invention relates to the provision of an integrated construction wherein an otherwise conventional front lens of an imaging transducer includes an extended portion or lip which is sealed to the probe front housing or case so as to form a separation wall between the coupling fluid of the liquid bath and the exterior of the housing in such a manner as to avoid undesirable acoustic effects associated with conventional separation membranes which are typically disposed over the transducer surface, as well as to overcome any fluid leaking problem due to the presence of bonding joints between the transducer and the membrane.

A further aspect of the invention concerns the provision of a method for shaping the extended portion or lip of the lens in the space separating the transducer and the probe housing or case so as to minimize resistance forces occurring at extreme positions of the transducer.

Yet another aspect of the invention concerns the ability of the transducer to be moved in various movement patterns or shapes such as swinging or tilting, rotating or sliding, with no change in the basic principles of the invention.

Further features and advantages of the present invention will be set forth in, or apparent from, the detailed description of preferred embodiments thereof which follows.

DESCRIPTION OF THE PREFERRED EMBODIMENTS OF THE INVENTION

Figure 1A:
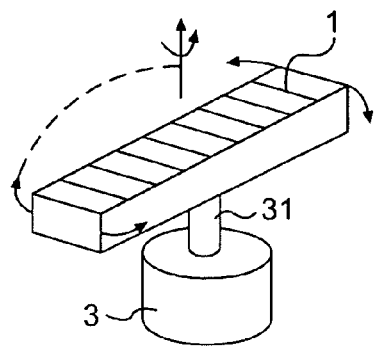
FIGS. 1A to 1C are perspective views of different prior art devices providing different movements of mechanical moving probes.
Figure 1B:
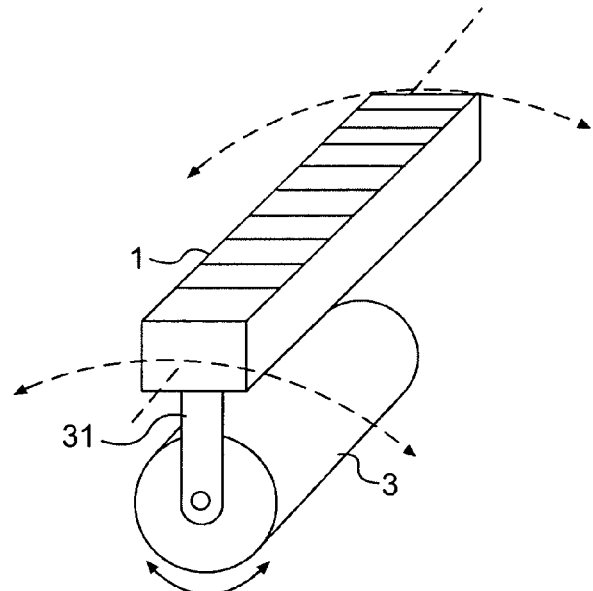
Figure 1C:
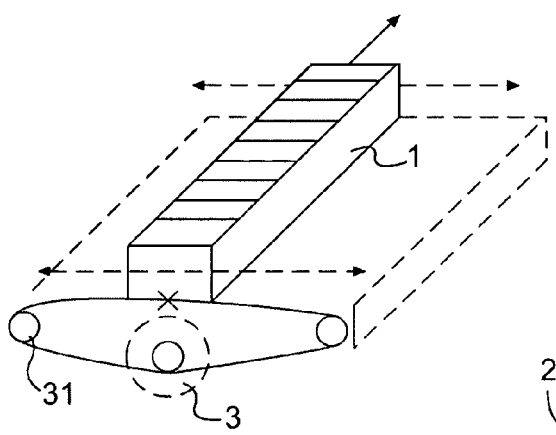

FIGS. 1A to 1C, in which the same reference numerals are used to denote similar elements, depict currently used prior art devices and illustrate conventional methods for moving an array transducer in order to obtain volume information. The array transducer 1 is used to provide planar electronic scanning images (i.e., 2D images) while the movement of the transducer 1 completes the acquisition of volume information.

In FIG. 1A, transducer 1 rotates in alternating fashion under the control of an energizing of motor 3 which is connected to the transducer 1 by a motor shaft 31. The transducer 1 is coupled to the motor shaft 31 at its center of symmetry so as to simplify rendering of the volume information. The direction of acoustic energy propagation from transducer 1 is controlled by rotation of the transducer 1 about the vertical axis that is superimposed on the axis of symmetry of transducer 1. This method of scanning is well developed and is convenient for use with moving phased array transducers which exhibit a rectangular footprint. As already mentioned above in the description of the prior art, phased array based 3D probes are particularly useful in cardiology for diagnoses wherein a wide angle of view and a small footprint are required.

FIG. 1B illustrates a variation of a moving linear array probe wherein transducer 1 is mounted longitudinally, along with a motor 3. The latter is energized alternatively to swing the transducer 1 forwardly and backwardly through means of a coupling arm 31 laterally coupled to the array transducer 1, as shown. With this method, the array transducer 1 is moved laterally in elevation so as to provide sector scanning of the volume to be imaged. Probes using this method are well suited to abdominal or general purpose imaging wherein the use of a linear (flat or curved) array transducer is indicated. It is noted that the width dimension of the acoustic window, and inherently, the effective movement of the associated probe will be determined by the length of arm 31 and the amplitude of the rotation of the array transducer 1.

FIG. 1C shows yet another method for providing transducer movement. In this method, transducer 1 is of an elongate or linear shape and slides along a major axis thereof, and along the elevation dimension of the transducer 1 in order to cover a desired scanning volume. Transducer 1 is attached to a motor 3 by a pulley-belt system 31 such as those used on a conveyer. Such a method has been developed for large area scanning applications such as breast imaging. Further, the size of the scanning footprint is only limited by the length of the transducer and the sliding amplitude of the device.

It should be understood that any or all of these methods of moving a transducer can be employed in implementing the present invention without departing from the scope and spirit of the invention as claimed.

However, in one preferred embodiment, a curved linear array transducer coupled with a motorized swinging mechanism to provide volumetric scanning is employed, and this embodiment is used as a non-limiting example in the description of the present invention.

Figure 2:
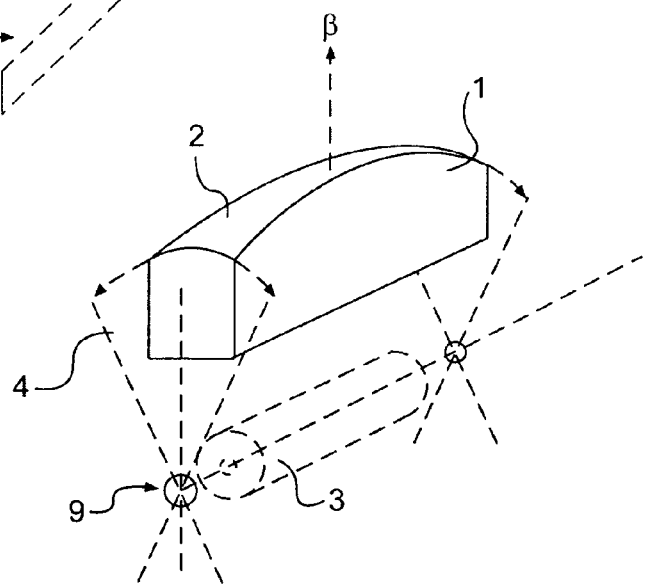
FIG. 2 is a perspective view of a moving probe used in discussing principles of the present invention.

Referring to FIG. 2, there is shown a transducer moving system wherein transducer 1 is elongate or of linear shape and includes one or several rows of transducer elements arranged along with the azimuth thereof. Transducer 1 is mounted on a swinging mechanism 9 (which is schematically illustrated by dashed lines) including a motor 3 which provides alternate rotation or swinging movement of transducer 1 about an axis parallel to the azimuth axis of the transducer. The vertical axis (indicated at z) represents the axis of symmetry of the acoustic plane. Transducer 1 includes a focusing front face 2 at which ultrasound waves directed to, and coming back from, the interrogative media are processed.

The transducer 1 is precisely mounted on the swinging mechanism 9 and the latter defines a rotation axis located underneath the transducer 1. Such a swinging system or mechanism imparts a lateral sector scanning movement to transducer 1 within a predetermined scanning angle, denoted 4, and defined by the sector delimited by dashed lines in FIG. 2.

The motor or motorization means 3 is preferably connected to the swinging mechanism 9 in such a manner that the output shaft of motor 3 is aligned with the rotation axis of the swinging mechanism, 9. However, although FIG. 2 shows motor 3 aligned with the output rotation axis of mechanism 9, this configuration is not required to achieve the movement of transducer 1 illustrated in FIG. 2. On the other hand, this configuration has the advantage of minimizing the number of intermediate coupling elements between the transducer 1 and motor 3. For simplicity of construction, it is desirable to position the motor shaft coaxial with the axis of rotation the mechanism and to extend the length of the motor shaft through use of coupling arm secured to the transducer 1.

A gearbox (not shown) for controlling motor speed and torque can also be used. In addition, a position encoder (not shown) can be positioned at or on the axis of rotation of the transducer 1 or at or on the motor output to provide accurate control of the transducer movement.

A preferred embodiment of invention is shown a particular moving mechanism. Transducer 1, having a straight linear or curved linear shape, is mounted on a pair of support members 15 by first and second connecting arms 31 that are attached to opposite ends of transducer 1. More at one end thereof on one of the support members 15 while one end of the other arm 31 is attached to the transmission shaft (shown in dashed lines at 3*a*) of motor 3. In the illustrated embodiment, shaft 3*a* is mounted in axial alignment with the axis of rotation 16 of transducer 1.

Figure 2A:
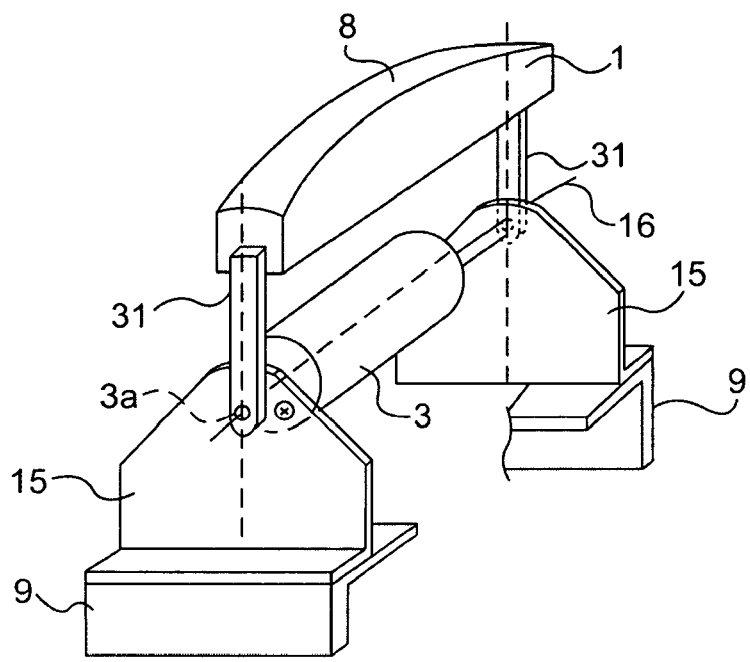
FIG. 2A is a perspective view of a moving probe based on these principles and constructed in accordance with a preferred embodiment of the invention.

The assembly of support members 15, arms 31, motor 3 and transducer 1 form a unit that can be mounted independently prior to integration thereof into the overall mechanism schematically illustrated at 9 in FIG. 2A. Although for clarity of illustration, FIG. 2A shows two separate support members 15 that are assembled on mechanism 9, it is generally desirable to provide a single piece support, i.e., a support wherein support members 15 form an integral unit, so as to improve the stiffness and precision of the system. The angular position of transducer 1 can be monitored by an encoding device (not shown) for sensing either the movement of the transducer 1 or that of the motor shaft 3*a*. The motor 3 is alternatively energized to rotate in clockwise and counterwise directions and to thus produce oscillating movement of the arms 31 over a limited angle typically ranging between 45 and 90 degrees. However, oscillations through an angle up to 180 degrees is feasible depending upon application requirements.

Figure 2B:
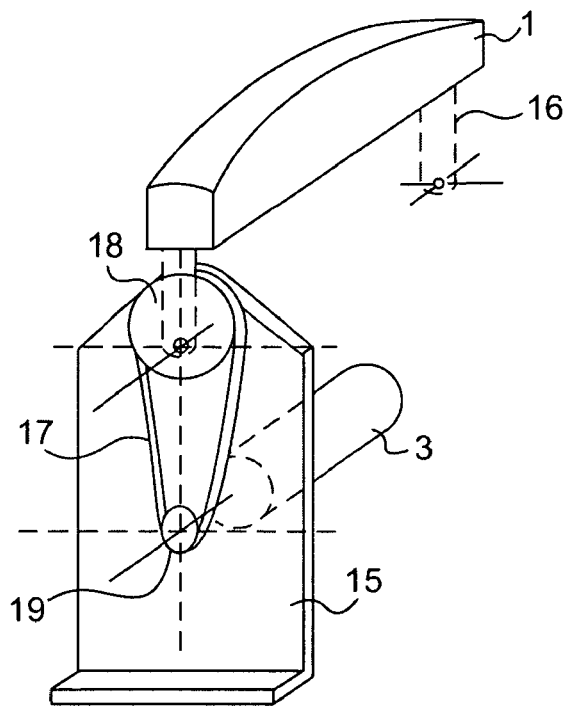
FIG. 2B is a perspective view of a moving probe constructed in accordance with a further preferred embodiment of the invention.

In some circumstances, e.g., wherein the size of the motor 3 is limited because of miniaturization constraints, a gearbox (not shown) or pulley system (not shown in FIG. 2A) can be added to the system to provide the desired oscillation performance. In this regard, referring to FIG. 2B, motor 3 is connected to transducer 1 through pulley-belt system including a first pulley 19 mounted on the motor shaft 3*a* and a second pulley 18 mounted on the axis of rotation of the transducer 1. Pulleys 18 and 19 are linked together by belt 17 which, in one embodiment, comprises a clutched transmission belt connected to the pulleys 18 and 19 in such a manner as to avoid a sliding effect with respect to the pulleys 18 and 19. Another advantage associated with a pulley-belt system of this type is that the distance between the front face of transducer 1 and the rotation axis can be minimized (since, i.e., an empty space can be provided between the two ends of the rotation axis).

Figure 3:
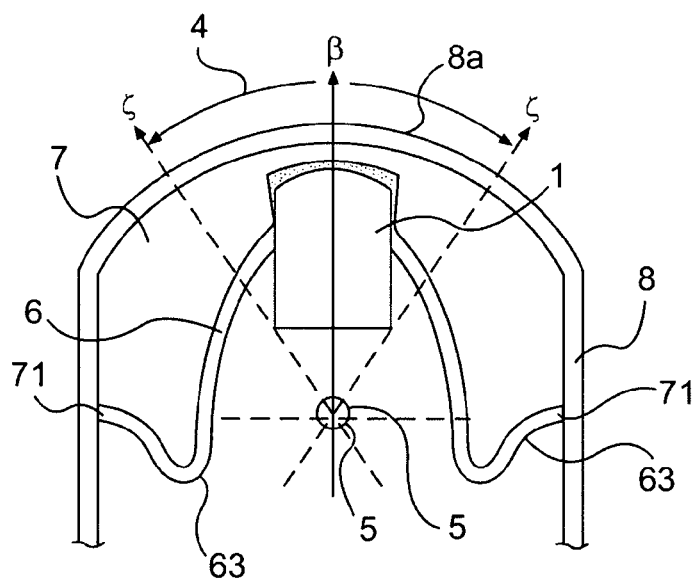
FIG. 3 is a cross-sectional view of a probe similar to that of FIGS. 2A and 2B and including a transducer, shell and lens extension in accordance with another preferred embodiment of the invention.

Referring again to the assembly of the array transducer into the probe housing according to some of the main objectives of the invention, in FIG. 3, wherein a cross-sectional view of a 3D probe including an array transducer 1 is shown, transducer 1 is shown in cross section so as to show transducer 1 in elevation and the axis of rotation thereof, denoted 5, therebeneath. The transducer 1 and its rotation mechanism are mounted inside of a probe housing 8 comprising a front convex curved or curved protruding portion 8*a* (at the top of housing 8 as viewed in FIG. 3) which acts as acoustic window for the transducer 1. Because the ultrasonic energy produced by transducer 1 is propagated into biologic tissue, it is therefore desirable that the acoustic impedance of window 8*a* be as close as possible to that of the human body, i.e., 1.6-1.8 MRayls. These characteristics can be realized by making window 8*a* out of polymeric materials such as HD Polyethylene or Polysulfone™ or the like.

As shown in FIG. 3, the transducer 1 is carried to oscillate so as to scan a sector 4 defined by dashed arrows (z). The angle spanned by sector 4 is selected based on the requirements of diagnostic operations to be carried out and can be modified, e.g., by using software for controlling the transducer movement, provided that this angle does not exceed the maximum sector angle permitted by the particular mechanical construction.

The space between the transducer 1 and the probe window 8*a* is filled with a coupling liquid 7. The latter is sealed within housing 8 by a sealing membrane 6 that, in one preferred embodiment, forms a part of, or is an extension of, a silicon lens (not shown in FIG. 3) provided on the front face of transducer 1. Membrane 6 has a continuous surface which is sealed to the probe housing 8 at the periphery 71 in such a manner as to ensure perfect sealing of the probe. In other words, membrane 6 passes over the front face of transducer 1 and the peripheral edges thereof are sealed in a leakproof manner to the probe housing 8. Further, the dimensions of membrane 6 are selected in accordance with the space available inside the housing probe 8 in a manner such as to result in the formation of a folding portion 63 of membrane 6 once the membrane 6 is secured to the transducer and probe. It is important to note that this approach requires the folding portion 63 of membrane 6 to be located underneath the axis of rotation 5 about which transducer 1 oscillates. This membrane geometry enables the transducer 1 to oscillate, through the maximum amplitude provided for, without any constraint from membrane 6.

The preferred methods of forming and assembling membrane 6 will be described in more detail in connection with FIGS. 4 and 5.

Figure 4:
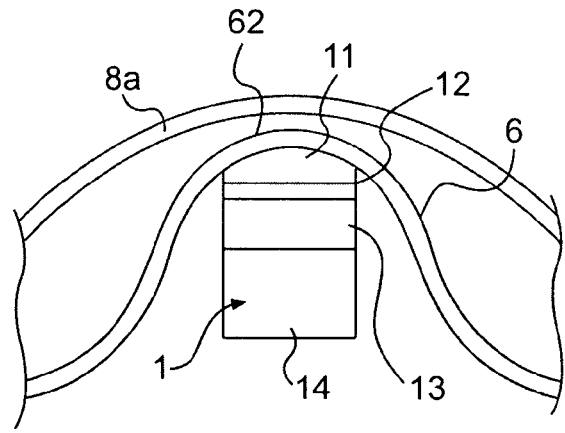
FIG. 4 is a cross-sectional view of a moving transducer having a separation membrane associated over its front surface, in accordance with a further preferred embodiment of the invention.

In FIG. 4, window 8*a* of the probe housing 8 forms, with membrane 6, a wet volume that is to be filled with a coupling liquid 7. Transducer 1, shown here in cross section, comprises a piezoelectric layer 13 which is sandwiched between, respectively, backing layer 14 and a matching layer 12. The matching layer 12 can be formed by a multilayered material so as to improve the energy transfer to the propagation medium. Backing layer 14 is preferably made up of an acoustically damped material such as a particle filled resin or polymer. One example of a suitable backing material is comprised of inorganic micron-sized particles mixed with high flexibility polyurethane resin.

The front face of transducer 1 is further equipped with a silicone focusing lens 11 having a transverse curvature in accordance with the desired focal length. In the embodiment of FIG. 4, the membrane 6 is bonded over the surface of the silicone lens 11 through an interface 62 which should be very thin, e.g., as thin as few microns, so as to not disturb the transducer impulse response. However, bonding interface 62 must be closely controlled and must be able to withstand the continuous oscillations of the transducer 1 that create substantial shearing forces exerted on the interface 62. A silicone adhesive system such as RTV 133 manufactured by General Electric Silicones is well suited for use in forming interface 62.

Figure 5:
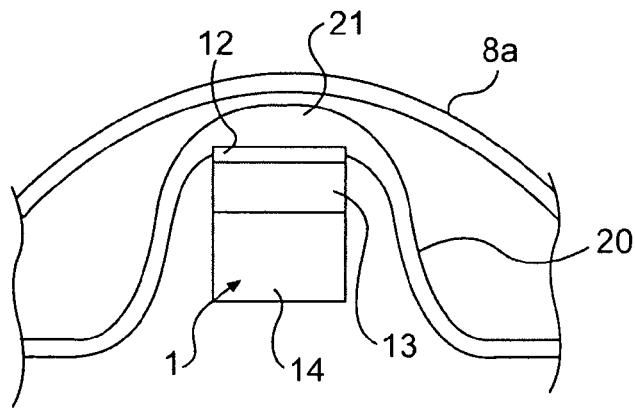
FIG. 5 is a cross-sectional view of a moving transducer having lens extension according to yet another embodiment of the invention.

Still another preferred embodiment of the invention is illustrated in FIG. 5 wherein the transducer 1 is similar to that of FIG. 4 but wherein elevational focusing of the transducer 1 is carried out by a silicone lens 21 which is disposed on the matching layer 12 and which includes a lens extension portion 20 surrounding the transducer 1. The periphery of lens extension portion 20 is sealed to the probe housing 8 so as to form a sealing cavity filled with a coupling fluid 7 as previously described. This approach has the advantage of avoiding the need for a bonding interface (corresponding to bonding interface 62 of FIG. 4) between the membrane (e.g., membrane 6 of FIG. 4) and the focusing lens (e.g., lens 11 of FIG. 4) which results in a lack of homogeneity and a decrease in the sensitivity of the associated transducer 1. Silicone lens 21 and the lens extension portion 20 can be provided either directly on the front face of transducer 1 using a molding process or can be manufactured separately and then assembled, by bonding, onto the transducer 1, using the same silicone rubber, in order to provide increased homogeneity and to increase the ease of the manufacturing process. The latter method of making lens 21 is more suitable for an industrial process when uniform high quantity is required, while the direct molding process is more convenient for prototypes.

Although the invention has been described above in relation to preferred embodiments thereof, it will be understood by those skilled in the art that variations and modifications can be effected in these preferred embodiments without departing from the scope and spirit of the invention.

What is claimed:

1. An ultrasonic swing probe for providing volume information with respect to a body organ, said probe comprising:
    a probe housing including an acoustic window enabling transmission of ultrasound energy therethrough;
    an array transducer disposed within the probe housing and having a front face;
    an undivided lens member including
    a front focusing lens disposed on the front face of said array transducer, and
    an extension membrane portions which extends from front focusing lens, which is made up of a same material as that of said front focusing lens, and which has a periphery sealed to said probe housing to form a hermetic cavity filled with a coupling fluid; and
    a drive means for providing a swinging movement of said array transducer.

2. An ultrasonic swing probe according to claim 1 wherein the linear array comprises a flat type array selected from the group consisting of a phased array and a conventional flat linear array.

3. An ultrasonic swing probe according to claim 1 wherein the linear array comprises a curved array.

4. An ultrasonic swing probe according to claim 1 wherein the linear array comprises a 1.5D array transducer.

5. An ultrasonic swing probe according to claim 1 wherein the focusing lens and extension membrane portions are comprised of latex.

6. An ultrasonic swing probe according to claim 1 wherein the focusing lens and extension membrane portions are comprised of silicone rubber.

7. An ultrasonic swing probe according to claim 1 wherein the transducer is rotated about a transducer rotation axis, and wherein said membrane portions includes a lateral folding portions located at a level beneath both the transducer rotation axis and the front face.

* * * * *

UNITED STATES PATENT AND TRADEMARK OFFICE
CERTIFICATE OF CORRECTION

PATENT NO. : 7,588,540 B2
APPLICATION NO. : 11/101526
DATED : September 15, 2009
INVENTOR(S) : Nguyen-Dinh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this

Twenty-first Day of September, 2010

David J. Kappos
*Director of the United States Patent and Trademark Office*